(12) United States Patent
Drennan

(10) Patent No.: US 7,476,185 B2
(45) Date of Patent: Jan. 13, 2009

(54) DYNAMIC HIP STABILIZER

(76) Inventor: Denis Burke Drennan, 4 Milburn Park, Evanston, IL (US) 60201

( * ) Notice: Subject to any disclaimer, the term of this patent is extended or adjusted under 35 U.S.C. 154(b) by 806 days.

(21) Appl. No.: 10/604,993

(22) Filed: Aug. 29, 2003

(65) Prior Publication Data

US 2004/0116260 A1   Jun. 17, 2004

Related U.S. Application Data

(60) Provisional application No. 60/319,519, filed on Sep. 4, 2002.

(51) Int. Cl.
*H63B 69/00* (2006.01)
(52) U.S. Cl. ..................... 482/124; 482/121; 601/123
(58) Field of Classification Search .............. 128/98.1, 128/101.1, 891, 889, 873, 876; 602/67–73; 482/121, 124; 2/383, 227, 242, 78.1–78.4, 2/22–24; 450/94
See application file for complete search history.

(56) References Cited

U.S. PATENT DOCUMENTS 2,035,010 A * 3/1936 Rawlings ................. 601/23

| 4,524,760 | A | * | 6/1985 | Lerner | 128/845 |
| 5,573,487 | A | * | 11/1996 | Wallner | 482/124 |
| 5,792,034 | A | * | 8/1998 | Kozlovsky | 482/124 |
| 6,629,912 | B2 | * | 10/2003 | Downs | 482/124 |

OTHER PUBLICATIONS

Eur Med Rehabilitation Center Adeli Suit Dec. 1992 e-mail euromed @ telbank.pl.*

* cited by examiner

*Primary Examiner*—Jerome Donnelly
(74) *Attorney, Agent, or Firm*—Hartman & Hartman, P.C.; Gary M. Hartman; Domenica N. S. Hartman

(57) ABSTRACT

A dynamic hip stabilizer utilized to prevent postoperative and recurrent traumatic hip dislocations. The stabilizer includes a pelvic girdle defining an upper opening for the wearer's waist and a lower opening for the wearer's hips, at least one thigh cuff defining an upper opening for a thigh of the wearer and a lower opening for a lower region of the wearer's thigh, and elastic cables attached to the pelvic girdle and the thigh cuff and extending therebetween in a longitudinal direction of the stabilizer. The stabilizer further includes channeling features associated with the pelvic girdle for guiding and controlling movement of the cables in directions transverse to the longitudinal direction of the stabilizer. The stabilizer may optionally include lateral extensions that connect the girdle to each thigh cuff.

19 Claims, 4 Drawing Sheets

DYNAMIC HIP STABILIZER

CROSS REFERENCE TO RELATED APPLICATIONS

This application claims the benefit of U.S. Provisional Application No. 60/319,519, filed Sep. 4, 2002.

BACKGROUND OF INVENTION

1. Field of the Invention

The present invention relates to devices utilized to prevent postoperative hip dislocations and recurrent traumatic hip dislocations. More particularly, this invention relates to a dynamic hip stabilizer with a combination of components that generate tensile forces capable of holding a patient's thigh with enough tension to control excessive adduction, flexion or extension, control excessive internal or external rotation, provide hip stability by controlling and modifying certain hip motions through increasing tension as the extremes of a particular motion are approached, and provide hip stability by constantly maintaining elevated abductor tension across the hip joint.

2. Description of the Related Art

There are a variety of techniques currently in use to prevent postoperative hip dislocations, recurrent traumatic hip dislocations, etc., some of which make use of specialized devices. A basic technique is to place a pillow between the thighs of the patient to cause abduction of the hips. A slightly more advanced technique is to secure a foam abduction pillow between the thighs with hook and loop straps to hold the hips in wide abduction. More advanced techniques include the use of single hip spica abduction braces, which generally comprise a thermoplastic waist brace attached to a thermoplastic thigh component by a hinged metal bar. The metal hinge portion allows flexion of the hip within a variable fixed range which can be set by the treatment provider. Single and bilateral hip spica casts, which serve to prevent all hip motions, also have long been used. Another type of device is the hip abduction brace, which generally comprises two curved semicircular plastic plates connected by hinges to a central threaded expansion-contraction device. By turning a central control threaded screw, the semicircular plastic plates spread out. When held between the proximal thighs by hook and loop straps, the device pushes the thighs apart, attempting to maintain abduction of the hips.

Various shortcomings are associated with the use of the above techniques and devices. Conventional pillows are too moveable and not wide enough to give consistent abduction, and undesirably allow the patient to move about. As a result, a pillow is rarely capable of preventing postoperative dislocation because it does not move with the patient who rolls over, or when the patient sits at the side of the bed or is being transferred to a wheel chair. Foam abduction pillows are clumsy and require considerable nursing effort to roll a patient from side to side. Furthermore, foam abduction pillows must be removed when the patient sits up and when bed-to-chair transfers are required.

A significant shortcoming of hip spica casts is the risk of prolonged stiffness because of the lack of all motion at the hip for many weeks. While single hip spica abduction braces avoid this concern, they require measurement and fitting by an orthotist and are formed from prefabricated parts of thermoplastic material and metal struts. Though single hip spica abduction braces can be worn in bed and while the patient sits and is being transferred, form-fit plastic abdominal and thigh portions of the brace often do not fit well, and allow many patients to rotate, putting the hip at risk. These braces also often allow some adduction and internal rotation, which is a significant risk to hip stability. Furthermore, this type of brace offers no compression of the femur against the pelvic acetabulum.

Hip abduction braces work reasonably well for the first days after surgery when the patient is fairly inactive. However, if not maintained in its fully abducted position, this type of brace allows for adduction to neutral and flexion is uncontrolled. The brace is removed for perineal care and when sitting the patient up at bedside. In addition, this type of brace cannot be worn during patient bed-to-wheelchair transfers or during gait training.

Other techniques and braces that pertain to the prevention of hip dislocations, or more generally to supporting or bracing the hip region, include U.S. Pat. No. 976,564 to Goodson, U.S. Pat. No. 1,722,192 to Brokaw, U.S. Pat. No. 2,332,119 Springer, U.S. Pat. No. 4,531,515 to Rolfes, U.S. Pat. No. 4,709,692 to Kirschenberg et al., U.S. Pat. No. 4,901,710 to Meyer, U.S. Pat. No. 4,905,678 to Cumins et al., U.S. Pat. No. 4,926,845 to Harris, U.S. Pat. No. 5,267,928 to Barile et al., U.S. Pat. No. 5,286,251 to Thompson et al., U.S. Pat. No. 5,465,428 to Earl, U.S. Pat. No. 5,840,050 to Lerman, U.S. Pat. No. 5,893,367 to Dubats et al., U.S. Pat. No. 5,928,175 to Tanaka, and U.S. Pat. No. 6,039,707 to Crawford et al. Each of Goodson, Brokaw, Barile et al. and Earl entail device with a waist portion, thigh portions, and elastic straps that interconnect the waist and thigh portions. Goodson's straps are limited to the posterior to provide posture support. Brokaw discloses a brace with inelastic anterior straps and elastic posterior straps. Barile et al. disclose a one-piece support garment with elastic anterior and posterior straps and elastic lateral straps, the latter of which may be wrapped in various ways around the thighs or hips of the wearer. Finally, Earl discloses an exercise device whose elastic straps are limited to the posterior side of the device.

It would be desirable if an improved device was available that was specifically configured to prevent hip dislocations by controlling excessive adduction, flexion and/or extension, controlling excessive internal or external rotation, increasing hip stability.

SUMMARY OF INVENTION

The present invention provides a dynamic hip stabilizer utilized to prevent hip dislocations, including postoperative and recurrent traumatic hip dislocations. The stabilizer generally comprises a pelvic girdle defining an upper opening for the wearer's waist, at least one thigh cuff defining a lower opening for a lower region of the wearer's thigh, and elastic cables attached to the pelvic girdle and the thigh cuff and extending therebetween in a longitudinal direction of the dynamic hip stabilizer. The stabilizer further includes channeling means associated with the pelvic girdle for guiding and controlling movement of the elastic cables in the longitudinal direction of the stabilizer and for inhibiting movement of the elastic cables in directions transverse to the longitudinal direction of the stabilizer. The channeling means preferably operate to control the paths of the cables in a manner that promotes their effect while preventing them from causing discomfort to the wearer. Additional and preferred features of the invention include lateral extensions that connect the girdle to each thigh cuff, and configuring the girdle and thigh cuffs to have opposing frustroconical shapes to inhibit movement of the girdle and thigh cuffs toward each other.

According to a preferred aspect of the invention, the tensile forces generated by the multiple elastic cables are capable of holding the wearer's thigh with enough tension to control excessive adduction, flexion or extension, provide hip stability by controlling and modifying certain hip motions through increasing tension as the extremes of a particular motion are approached, and provide hip stability by constantly maintaining elevated abductor tension. The girdle and thigh cuff are configured to permit attachment and positioning elastic cables of potentially different lengths in multiple directions to generate different tensions, thereby enabling the stabilizer to provide a range of stabilizing forces. The girdle and thigh cuff are also preferably configured to permit attachment of one or more cables from the posterior of the girdle to the anterior of the thigh cuff, enabling control of excessive internal or external rotation. The channeling means make such configurations possible without discomfort to the wearer.

Other objects and advantages of this invention will be better appreciated from the following detailed description.

DETAILED DESCRIPTION

Figure 1:
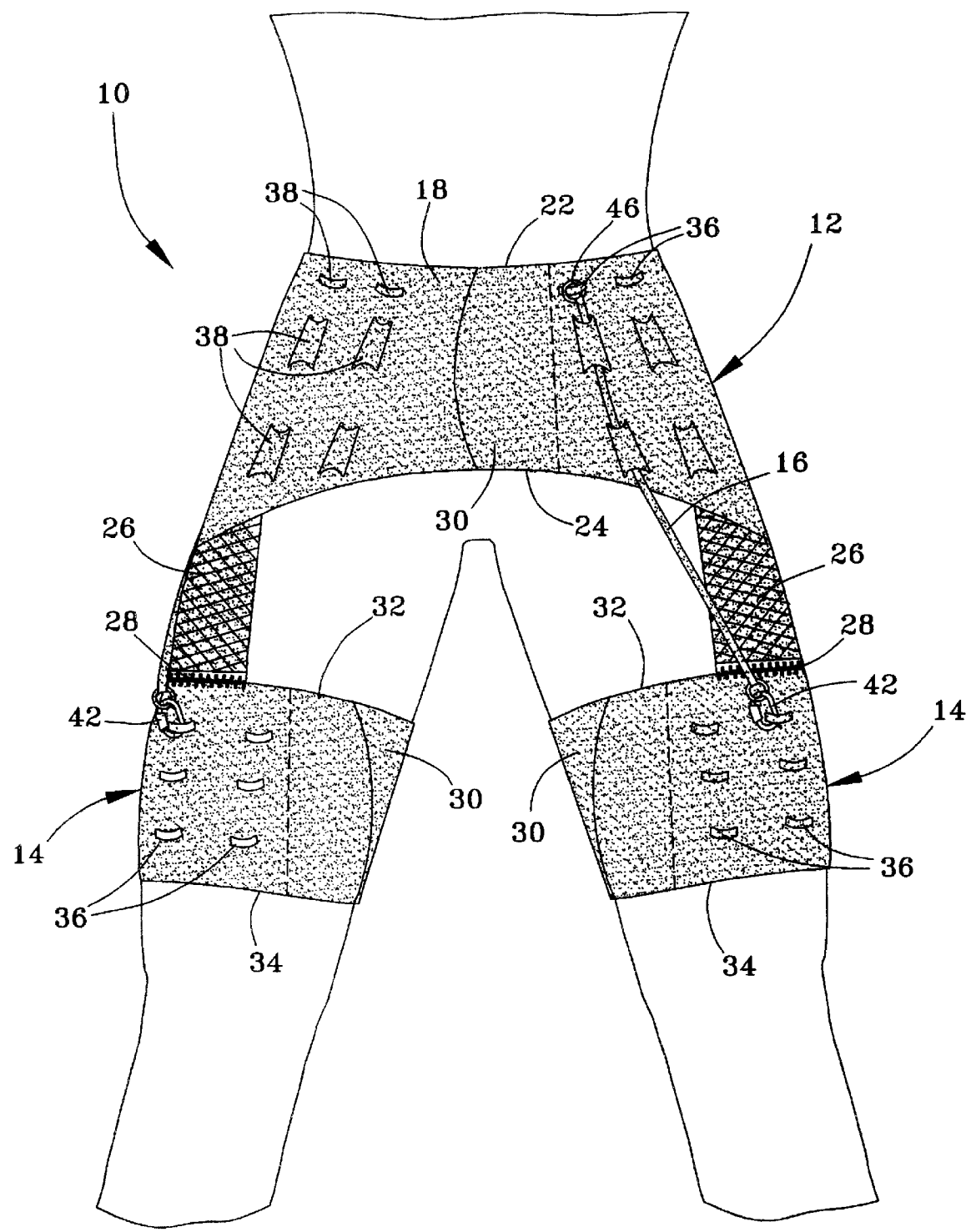
FIGS. 1, 2 and 3 represent anterior, lateral and posterior views, respectively, of a patient wearing a dynamic hip stabilizer in accordance with a preferred embodiment of the invention.

FIGS. 1 through 5 show a dynamic hip stabilizer 10 in accordance with the present invention as comprising three primary components: a pelvic girdle 12, thigh cuffs 14 (at least one, preferably two), and elastic cables 16. The cables 16 are shown connected to the girdle 12 and the thigh cuffs 14 so as to be under elastic tension, such that the cuffs 14 prevent rotation of the girdle 12 as a result of the force generated by the cables 16. In some patients, only the operative thigh cuff 14 may be necessary.

The girdle 12 and thigh cuffs 14 preferably comprise a flexible but firm outer layer 18 of fabric material sewn or adhered to an inner lining material 20 that is preferably soft and nonirritating to the skin. The outer layer 18 is preferably relatively stiffer than the inner lining material 20 to provide support to the lining material 20. The inner lining material 20 preferably has a high skin friction equivalent, i.e., resists slippage against the skin, a particularly suitable example of which is commonly referred to as polar fleece. A suitable material for the outer layer 18 is plastic-molded polyester mesh.

As evident from the Figures, the girdle 12 is narrower at an upper opening defined by its upper extent 22 (corresponding to the waist level of the wearer) and wider at a lower opening defined by its lower extent 24 (corresponding to the pelvic-hip level of the wearer), so as to have a frustroconical shape. As shown, the inner lining material 20 may project beyond the upper extent 22 of the girdle 12 for added comfort to the wearer. In addition, extensions 26 of the inner lining material 20 project below the outer layer 18 at the lateral portions of the girdle 12 to extend distally along the midlateral of each thigh, preferably for about three to about five inches (about eight to about thirteen cm) below the outer layer 18, and are releasably connected with zippers 28 (or other suitable releasable fastener) to the thigh cuffs 14. The extensions 26 serve to inhibit slippage and motion between the wearer and the stabilizer 10, inhibit hip flexion, limit rotation of the thigh cuffs 14 when under elastic rotational tension, and help maintain the distance relationship between the girdle 12 and cuffs 14. Similar to the girdle 12, each of the thigh cuffs 14 is frustroconical-shaped, though inverted relative to the girdle 12 so as to be wider at an upper opening defined by its proximal-top extent 32 and narrower at a lower opening defined by its inferior-bottom extent 34 in accordance with the shape of the human thigh. With this arrangement, the girdle 12 and thigh cuffs 14 are inhibited from moving toward each other under the tension generated by the cables 16. The girdle 12 and the thigh cuffs 14 are preferably closable with hook-and-loop-closures 30 (or another suitable releasable fasteners), so that the upper and lower openings of the girdle 12 and thigh cuffs 14 can be appropriately sized for the wearer. The closures 30 of the thigh cuffs 14 are preferably located over the inside of the wearer's thighs when the stabilizer 10 is worn.

As evident from FIGS. 1 through 4, the girdle 12 and thigh cuffs 14 are equipped with series of loops 36. A single transverse row of loops 36 is shown as located near the upper extent 22 of the girdle 12, extending around nearly the full circumference of the girdle 12 while avoiding the hook-and-loop closure 30 (FIG. 1). The transverse loops 36 of the girdle 12 are preferably spaced apart about every two and one-half inches (about six cm). FIGS. 1 through 4 show each thigh cuff 14 as being provided with three rows of the transverse loops 36 vertically spaced apart in the longitudinal direction of the stabilizer 10, with each row extending about three quarters of the circumference of each thigh cuff 14 to avoid the hook-and-loop closures 30 located at the inner thigh. While the girdle 12 is shown with a single transverse row of loops 36 and the thigh cuffs 14 are shown with three transverse rows of loops 36, any number of rows and loops 36 could be used. In particular, the lower row of loops 36 on the cuffs 14 are believed to be optional, as under certain conditions a cable 16 attached to a loop 36 near the lower extent 34 of a cuff 14 may cause the cuff 14 to curl toward the girdle 12. Finally, the loops 36 of the girdle 12 and cuffs 14 need not be aligned in rows.

As also evident from FIGS. 1 through 4, the girdle 12 is further equipped with a series of channel loops 38 arranged in longitudinal rows that are aligned with the transverse loops 36 and extend toward the lower extent 24 of the girdle 12 and thigh cuffs 14. The channel loops 38 can be formed of fabric to be of any suitable size, e.g., one and one-eighth inches (about 2.8 cm) wide and one and one-quarter inches (about 3.2 cm) long. While shown as raised loops, other channel-type configurations could be used, including more rigid tubes attached to the girdle 12 or channels recessed into or beneath the surface of the girdle 12. Each of the elastic cables 16 is attached to one of the transverse loops 36 of the girdle 12 and to one of the transverse loops 36 of the thigh cuffs 14, passing therebetween through one of the longitudinal rows of channel loops 38 on the girdle 12 so as to be guided and controlled by the channel loops 38. Simple "C" rings 40 or other appropriate connectors can be used to connect the proximal ends of the elastic cables 16 to the transverse loops 36 of the girdle 12, whereas quick links 42 or other releasable connectors preferably connect the cables 16 to the transverse loops 36 on the thigh cuffs 14. The quick links 42, well known and commercially available from a variety of sources, are covered with neoprene tubes that act as metal covers. It is foreseeable that quick links could be used in place of the "C" rings 40 at attach proximal ends of the cables 16.

Figure 2:
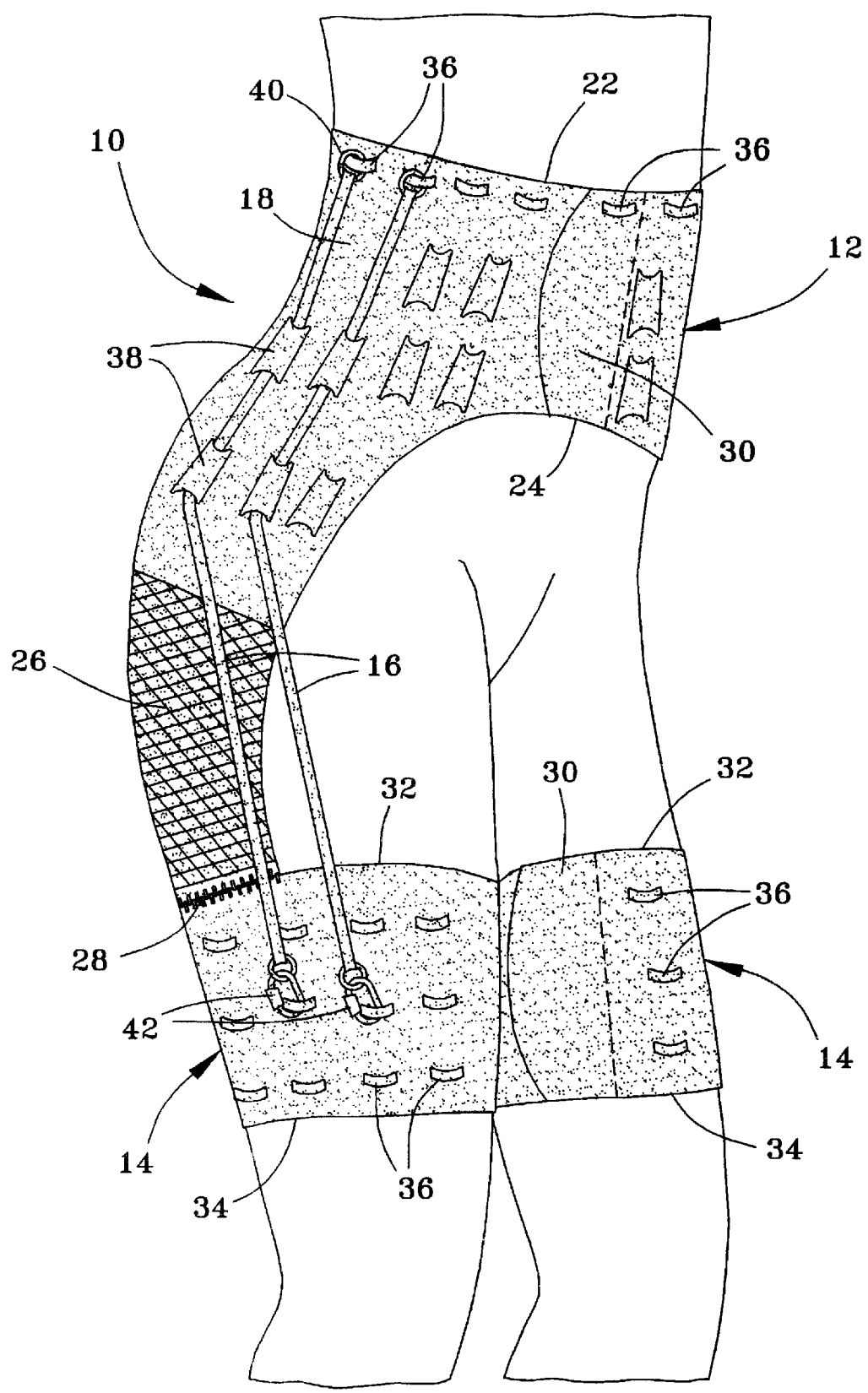
Figure 3:
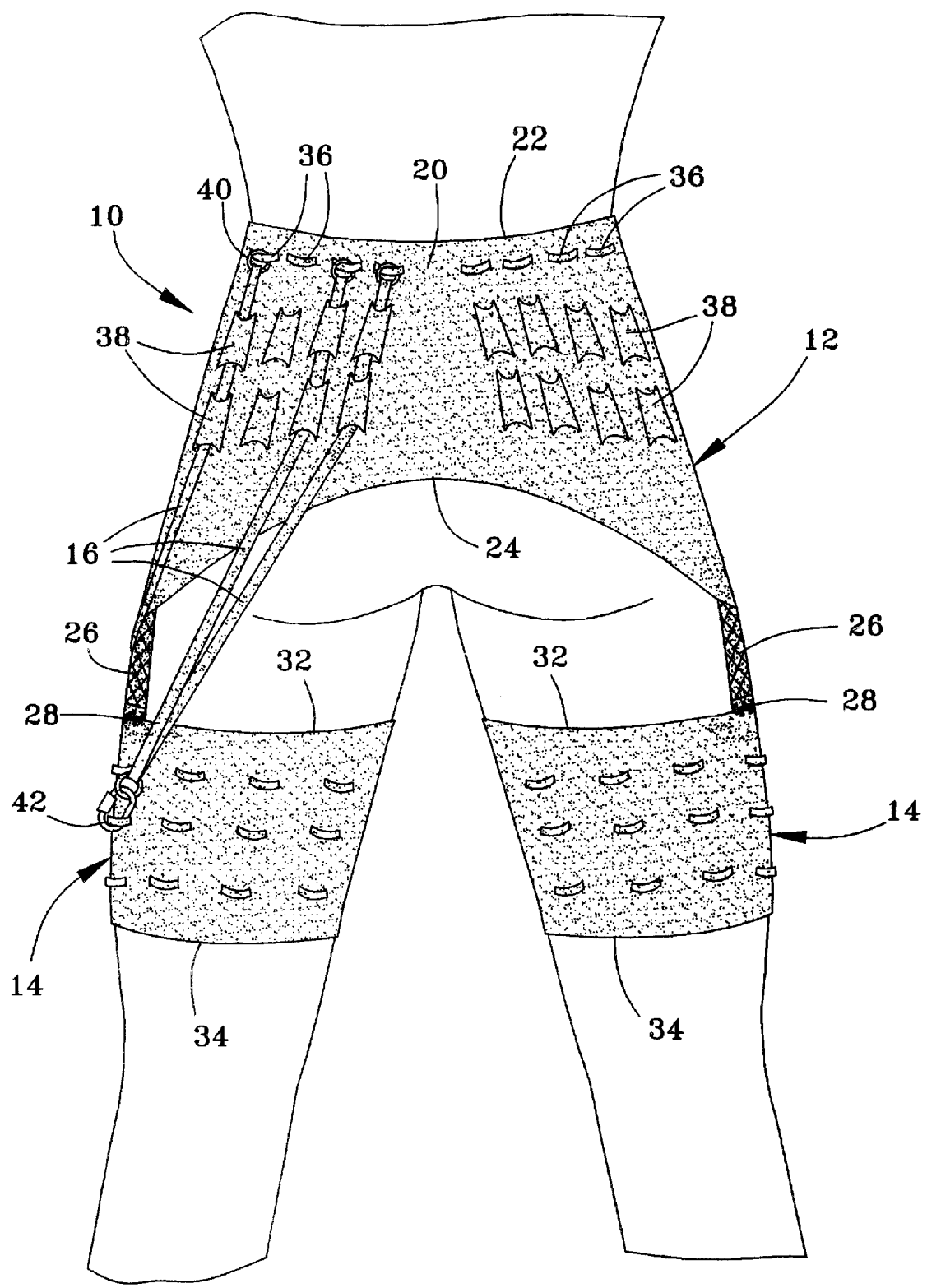
Figure 4:
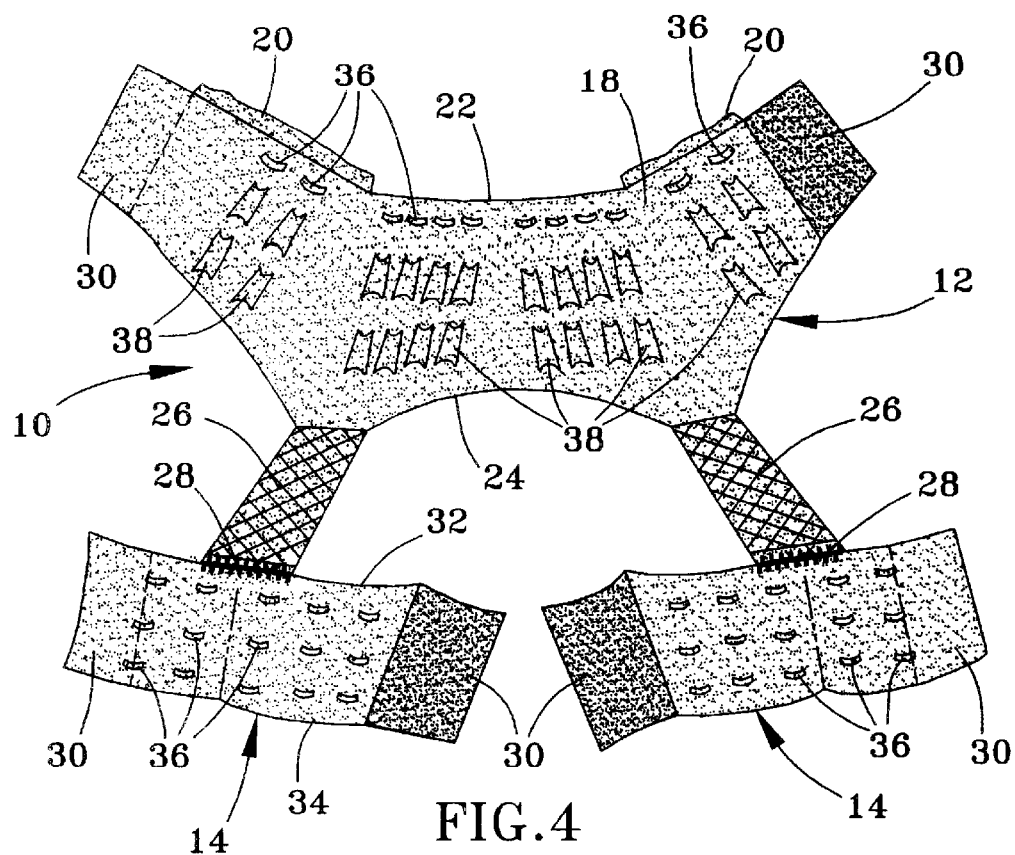
FIGS. 4 and 5 are plan views of the exterior and interior surfaces, respectively, of the dynamic hip stabilizer shown in FIGS. 1, 2 and 3.
Figure 5:
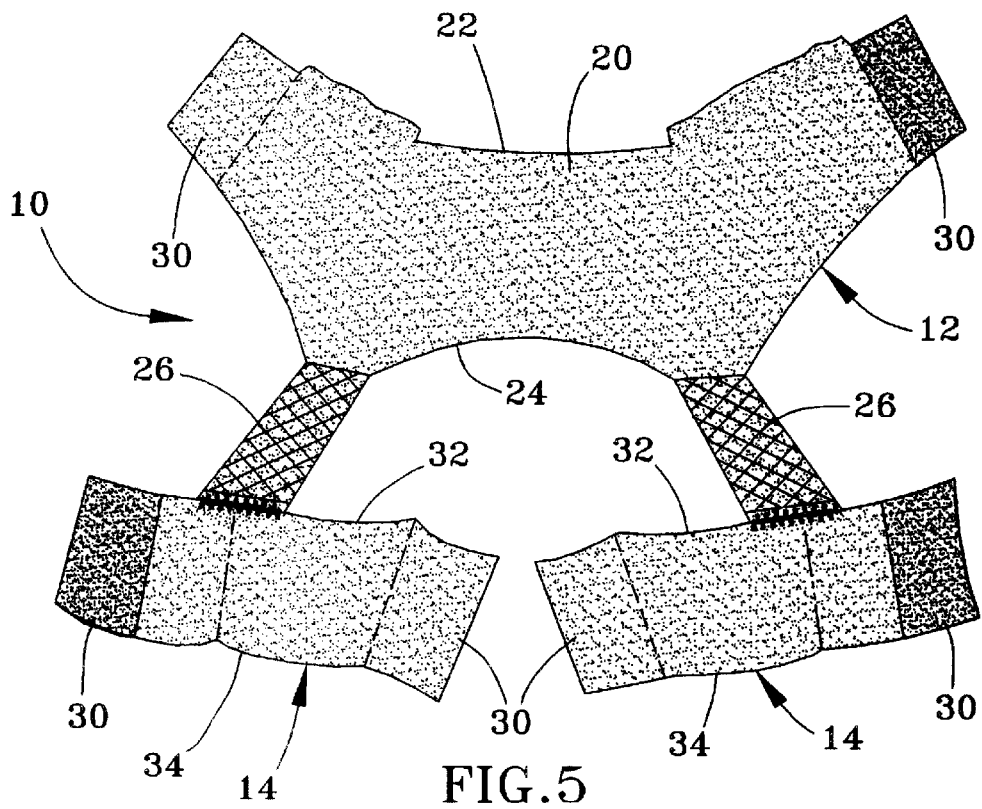

As evident from FIGS. 1 through 3, the channel loops 38 control the paths of the cables 16, directing the tension generated by the cables 16 along paths beneficial to the wearer. Simultaneously, the loops 38 prevent the cables 16 from moving in directions transverse to the longitudinal direction of the stabilizer 10, which would likely cause discomfort to the wearer. For example, the loops 38 are able to prevent the cables 18 rolling and snapping over the wearer's buttocks or catching in the gluteal cleft. In practice, a single transverse row of channel loops 38 near the lower extent 24 of the girdle 12 has been shown to be adequate, such that the row of channel loops 38 nearest the loops 36 can be considered as optional.

As evident from FIGS. 1 and 3, respectively, cables 16 can be routed between the anterior sides of the girdle 12 and cuffs 14 and between the posterior sides of the girdle 12 and cuffs 14. As represented in FIG. 2, cables 16 can also be routed from the posterior of the girdle 12 to the anterior or sides of the thigh cuffs 14. Beneficial effects associated with the ability to selectively establish different routes for the cables 16 include the capability of applying internal or external rotational forces. Anterior hip dislocations require an internal rotation and flexion force, while posterior dislocations require external rotation and an extension force. Lateral abductor deficiencies require an abduction force, which can also be generated by appropriately routing one or more cables 16. By varying the tensions and lengths of the cables 16, greater and lesser flexion or extension forces can be created.

The dynamic hip stabilizer 10 described above is able to solve various problems, shortcomings and disadvantages of the prior art. The stabilizer 10 eliminates motion between the wearer's skin and the stabilizer 10 by using custom-fitting girdle 12 and thigh cuffs 14 equipped with a soft, high-friction inner lining material 20. With the closures 30, the sizes/circumferences of the girdle 12 and thigh cuffs 14 can be individually tailored to allow for individual abdominal-thigh size variations. The cuffs 14 can then be individually attached to the girdle 12 with the zippers 28, thereby inhibiting slippage and motion between the wearer and the stabilizer 10. Multiple elastic cables 16 can be provided in multiple lengths and generate any number of different tension loads in multiple directions to provide the stabilizing forces required by the wearer's condition. In particular, the cables 16 can be routed between the girdle 12 and the thigh cuffs 14 so that the wearer's thigh is held to the pelvis with enough tension to control excessive adduction, flexion, and/or extension, control excessive internal or external rotation (by passing one or more cables 16 from back to front), provide hip stability by controlling and modifying certain hip motions through increasing tension as the extremes of a particular motion are approached, and provide hip stability by constantly maintaining elevated abductor tension and hip joint compression.

With the dynamic hip stabilizer 10 of this invention, the wearer can be allowed a full range of motion against an increasing tension, which increase strength and institutes proprioceptive feedback to create a muscle contraction throughout the range, thereby aiding the abductor muscles in keeping the hip in place. The constant tension and full range of motion should allow the wearer to move about in bed, sit safely at the side of the bed, and transfer safely to a wheelchair or commode. Unlike various other devices that are commercially available, the stabilizer 10 does not need to be removed for motion or activities. Furthermore, the open groin and buttock areas allow for urination and defecation without having to remove or adjust the stabilizer 10. Finally, the constant and adjustable tension generated by the cables 16 acts as a progressive resistive strengthening device to aid in postoperative rehabilitation.

While the invention has been described in terms of a preferred embodiment, it is apparent that other forms could be adopted by one skilled in the art. For example, the pelvic girdle 12 could be modified to use different materials, the cables 16 can be in the form of flat straps, round tubing, etc., the construction of the girdle 12 and thigh cuffs 14 could be simplified to use a single material, the 12 girdle could be in the form of a compression or plain pair of shorts with some form of elastic cables (straps) attached, and a stabilizer device having a similar function could be devised but with the connection between the pelvic girdle 12 and the thigh cuffs 14 eliminated. Therefore, the scope of the invention is to be limited only by the following claims.

The invention claimed is:

1. A dynamic hip stabilizer for preventing hip dislocation of a wearer, the stabilizer comprising:
   a pelvic girdle defining an upper opening for the wearer's waist and a lower opening for the wearer's hips;
   at least one thigh cuff defining lower and upper openings for the wearer's thigh;
   elastic cables attached to the pelvic girdle and the thigh cuff and extending therebetween in a longitudinal direction of the dynamic hip stabilizer to generate tensile forces therebetween;
   means at lateral regions of the pelvic girdle for flexibly connecting the pelvic girdle and the thigh cuff, limiting rotation of the thigh cuff when under the tensile forces of the elastic cables, and maintaining distance between the pelvic girdle and the thigh cuff; and
   channeling means associated with the pelvic girdle for guiding and controlling movement of the elastic cables in the longitudinal direction of the stabilizer and for inhibiting movement of the elastic cables in directions transverse to the longitudinal direction of the stabilizer;
   wherein the pelvic girdle and the thigh cuff each have a frustroconical-shape, and the upper opening of the pelvic girdle is narrower than the lower opening of the pelvic girdle and the lower opening of the thigh cuff is narrower than the upper opening of the thigh cuff such that the pelvic girdle and the thigh cuff are inhibited from moving toward each other under the tensile forces generated by the elastic cables.

2. The dynamic hip stabilizer according to claim 1, wherein each of the pelvic girdle and the thigh cuff comprises an outer layer of a fabric material overlying an inner layer of a soft lining material.

3. A dynamic hip stabilizer for preventing hip dislocation of a wearer, the stabilizer comprising:
   a pelvic girdle defining an upper opening for the wearer's waist;
   at least one thigh cuff defining a lower opening for the wearer's thigh;
   elastic cables attached to the pelvic girdle and the thigh cuff and extending therebetween in a longitudinal direction of the dynamic hip stabilizer; and
   channeling means associated with the pelvic girdle for guiding and controlling movement of the elastic cables in the longitudinal direction of the stabilizer and for inhibiting movement of the elastic cables in directions transverse to the longitudinal direction of the stabilizer;
   wherein each of the pelvic girdle and the thigh cuff comprises an outer layer of a fabric material overlying an inner layer of a soft lining material, and the dynamic hip stabilizer further comprises at least one extension comprising the soft lining material and free of the fabric material, the extension interconnecting the inner layer of the pelvic girdle and the thigh cuff at an outer lateral region of the wearer.

4. The dynamic hip stabilizer according to claim 1, wherein the channeling means comprises loops attached to the pelvic girdle and extending in the longitudinal direction of the dynamic hip stabilizer.

5. The dynamic hip stabilizer according to claim 4, wherein the loops are aligned in multiple rows in the longitudinal direction of the dynamic hip stabilizer.

6. The dynamic hip stabilizer according to claim 1, wherein at least one of the elastic cables passes from a posterior portion of the pelvic girdle to an anterior portion of the thigh cuff, the tensile forces generated by the at least one elastic cable controlling excessive internal or external rotation.

7. The dynamic hip stabilizer according to claim 1, wherein the elastic cables are not all of the same length.

8. The dynamic hip stabilizer according to claim 1, further comprising means for attaching the elastic cables to the pelvic girdle and the thigh cuff, the attaching means providing multiple attachment points for each of the elastic cables on each of the pelvic girdle and the thigh cuff so as to enable selective decreasing and increasing of the tensile force generated by each of the elastic cables.

9. The dynamic hip stabilizer according to claim 1, wherein the pelvic girdle and the thigh cuff are each equipped with hook-and-loop closures so as to permit adjustment of the sizes of the upper and lower openings thereof.

10. A dynamic hip stabilizer worn by a wearer to prevent hip dislocation of the wearer, the stabilizer comprising:

a pelvic girdle formed of an outer layer of a fabric material overlying an inner layer of a soft lining material, the pelvic girdle being narrower at an uppermost extent thereof to define an upper opening for the wearer's waist and being wider at a lowermost extent thereof to define a lower opening for the wearer's hips;

at least one thigh cuff formed of an outer layer of fabric material overlying an inner layer of a soft lining material, the thigh cuff being wider at an uppermost extent thereof to define an upper opening for a thigh of the wearer and being narrower at a lowermost extent thereof to define a lower opening for the wearer's thigh;

elastic cables attached to the pelvic girdle and the thigh cuff and extending therebetween in a longitudinal direction of the dynamic hip stabilizer, the elastic cables generating sufficient tensile forces to hold the wearer's thigh with enough tension to control excessive adduction, flexion and extension, provide hip stability by controlling and modifying hip motions through increasing tension as extremes of a hip motion are approached, and provide hip stability by maintaining elevated abductor tension;

means for attaching the elastic cables to the pelvic girdle and the thigh cuff, the attaching means providing multiple attachment points for each of the elastic cables on each of the pelvic girdle and the thigh cuff so as to enable selective decreasing and increasing of the tensile force generated by each of the elastic cables; and channeling means associated with the pelvic girdle for guiding and controlling movement of the elastic cables in the longitudinal direction of the stabilizer and for inhibiting movement of the elastic cables in directions transverse to the longitudinal direction of the stabilizer during movement of the wearer's hips and the wearer's thighs relative to the wearer's hips.

11. The dynamic hip stabilizer according to claim 10, wherein the channeling means comprises loops attached to the pelvic girdle and extending in the longitudinal direction of the dynamic hip stabilizer toward the lower opening of the pelvic girdle.

12. The dynamic hip stabilizer according to claim 11, wherein the loops are aligned in multiple longitudinal rows in the longitudinal direction of the dynamic hip stabilizer.

13. The dynamic hip stabilizer according to claim 10, wherein at least one of the elastic cables passes from a posterior portion of the pelvic girdle to an anterior portion of the thigh cuff, the tensile forces generated by the at least one elastic cable controlling excessive internal or external rotation.

14. The dynamic hip stabilizer according to claim 10, further comprising means at lateral regions of the pelvic girdle and releasably attached to the thigh cuff for connecting the pelvic girdle and the thigh cuff, limiting rotation of the thigh cuff when under the tensile forces of the elastic cables, and maintaining distance between the pelvic girdle and the thigh cuff.

15. The dynamic hip stabilizer according to claim 14 wherein the stabilizer comprises two of the thigh cuffs, a first of the connecting, limiting, and maintaining means is releasably attached to a first of the two thigh cuffs, and a second of the connecting, limiting, and maintaining means is releasably attached to a second of the two thigh cuffs.

16. The dynamic hip stabilizer according to claim 10, wherein each of the inner layers of the pelvic girdle and the thigh cuff has high skin friction equivalent.

17. The dynamic hip stabilizer according to claim 10, wherein the elastic cables are not all of the same length.

18. The dynamic hip stabilizer according to claim 10, further comprising means at lateral regions of the pelvic girdle for flexibly connecting the pelvic girdle and the thigh cuff, limiting rotation of the thigh cuff when under the tensile forces of the elastic cables, and maintaining distance between the pelvic girdle and the thigh cuff.

19. The dynamic hip stabilizer according to claim 10, wherein the pelvic girdle and the thigh cuff are each equipped with hook-and-loop closures so as to permit adjustment of the sizes of the upper and lower openings thereof.

* * * * *